(12) United States Patent
Noland

(10) Patent No.: US 12,017,938 B2
(45) Date of Patent: *Jun. 25, 2024

(54) COMPOSITION WITH A TIME RELEASE MATERIAL FOR REMOVING HALOGENATED HYDROCARBONS FROM CONTAMINATED ENVIRONMENTS

(71) Applicant: Remediation Products, Inc., Golden, CO (US)

(72) Inventor: Scott Noland, Arvada, CO (US)

(73) Assignee: Remediation Products, Inc., Golden, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/094,883

(22) Filed: Jan. 9, 2023

(65) Prior Publication Data
US 2023/0159363 A1 May 25, 2023

Related U.S. Application Data

(60) Division of application No. 16/686,561, filed on Nov. 18, 2019, now Pat. No. 11,548,802, which is a continuation-in-part of application No. 15/147,733, filed on May 5, 2016, now Pat. No. 10,479,711.

(51) Int. Cl.
| | |
|---|---|
| C02F 3/34 | (2023.01) |
| B09C 1/00 | (2006.01) |
| B09C 1/10 | (2006.01) |
| C02F 1/28 | (2023.01) |
| C02F 1/68 | (2023.01) |
| C02F 1/70 | (2023.01) |
| C12N 1/12 | (2006.01) |
| C12N 1/14 | (2006.01) |
| C12N 1/20 | (2006.01) |
| C02F 101/36 | (2006.01) |
| C02F 103/06 | (2006.01) |

(52) U.S. Cl.
CPC .............. *C02F 3/348* (2013.01); *B09C 1/002* (2013.01); *B09C 1/10* (2013.01); *C02F 1/288* (2013.01); *C02F 1/688* (2013.01); *C02F 1/705* (2013.01); *C12N 1/12* (2013.01); *C12N 1/14* (2013.01); *C12N 1/20* (2013.01); *B09C 2101/00* (2013.01); *C02F 1/281* (2013.01); *C02F 1/283* (2013.01); *C02F 2101/36* (2013.01); *C02F 2103/06* (2013.01)

(58) Field of Classification Search
None
See application file for complete search history.

(56) References Cited

U.S. PATENT DOCUMENTS

| | | | |
|---|---|---|---|
| 3,803,033 A | 4/1974 | Sutherland | |
| 4,478,954 A | 10/1984 | Connolly | |
| 4,713,343 A | 12/1987 | Wilson et al. | |
| 5,057,227 A | 10/1991 | Cohen | |
| 5,266,213 A | 11/1993 | Gillham | |
| 5,403,809 A | 4/1995 | Miller | |
| 5,411,664 A | 5/1995 | Seech | |
| 5,427,944 A | 6/1995 | Lee et al. | |
| 5,436,211 A | 7/1995 | Erbel | |
| 5,480,579 A | 1/1996 | Seech et al. | |
| 5,534,154 A | 7/1996 | Gillham | |
| 5,618,427 A | 4/1997 | Seech et al. | |
| 5,711,020 A | 1/1998 | Wolfe et al. | |
| 5,733,067 A | 3/1998 | Hunt et al. | |
| 5,750,036 A | 5/1998 | Sivavec | |
| 5,766,929 A | 6/1998 | Orolin et al. | |
| 5,833,855 A | 11/1998 | Saunders | |
| 6,001,252 A | 12/1999 | Rice et al. | |
| 6,008,028 A | 12/1999 | Bender et al. | |
| 6,083,394 A | 7/2000 | Seech et al. | |

(Continued)

FOREIGN PATENT DOCUMENTS

| | | |
|---|---|---|
| CN | 9529129 | 11/1995 |
| CN | 1668535 A | 9/2005 |

(Continued)

OTHER PUBLICATIONS

Extended European Search Report, Application No. 17792991.6-1014, PCT/US2017027384, Dated Nov. 21, 2019.
Chinese Office Action, for Application No. 201710257186.2, dated Apr. 6, 2020.
Ehrhardt, H. M., et al., "Phenol degradation by Microorganisms Adsorbed on activated carbon" Appl. Microbiol. Biotechnol (1985) 21:32-36.
Sakakibara, Yutaka, et al., "Biobarrier Comprised of Soil and BAC: Suppression of Greenhouse Gases" Activated Carbon and Other Support Media Used for Biobarriers, 113-118, The Sixth International in Situ and on-site Bioremediation Symposium: San Diego, CA 2001, ISBN: 9781574771107.

(Continued)

*Primary Examiner* — David W Berke-Schlessel
(74) *Attorney, Agent, or Firm* — Snell & Wilmer L.L.P

(57) ABSTRACT

A composition for remediation of soil and groundwater containing halogenated compounds. The remediation composition includes an elemental iron-based composition, which may include activated carbon capable of absorbing the halogenated compounds with numerous pores impregnated with elemental iron. The remediation composition further includes a first bioremediation material including a blend of one-to-many organisms capable of degrading the halogenated compounds. The remediation composition includes an organic compound or polymeric substance and a second bioremediation material including a blend of one-to-many organisms capable of degrading the organic compound or polymeric substance over time (e.g., 20 to 365 or more days to provide a time release substrate-creating material or platform) into smaller molecules or compounds used by the organisms in the first bioremediation material while degrading the halogenated compounds. The organic compound may be a complex carbohydrate such as food grade starch, chitin, or other complex carbohydrate such as one with low water solubility.

21 Claims, No Drawings

(56) References Cited

U.S. PATENT DOCUMENTS

| | | | |
|---|---|---|---|
| 6,150,157 | A | 11/2000 | Keasling et al. |
| 6,242,663 | B1 | 6/2001 | Ponder et al. |
| 6,337,019 | B1 | 1/2002 | Razavi-Shirazi |
| 6,382,537 | B1 | 5/2002 | Birke |
| 6,783,678 | B2 | 8/2004 | Sorenson |
| 6,787,034 | B2 | 9/2004 | Noland et al. |
| 7,045,339 | B2 | 5/2006 | Sorenson et al. |
| 7,129,388 | B2 | 10/2006 | Scalzi et al. |
| 7,141,170 | B2 | 11/2006 | Sorenson |
| 7,449,114 | B2 | 11/2008 | Sorenson |
| 7,531,709 | B2 | 5/2009 | Scalzi et al. |
| 8,097,559 | B2 | 1/2012 | Noland et al. |
| 8,618,021 | B2 | 12/2013 | Noland |
| 2002/0090697 | A1 | 7/2002 | Hince |
| 2004/0007524 | A1 | 1/2004 | Noland et al. |
| 2005/0006306 | A1 | 1/2005 | Noland et al. |
| 2007/0256985 | A1 | 11/2007 | Zhao et al. |
| 2008/0227179 | A1 | 9/2008 | Smith et al. |
| 2012/0114852 | A1 | 5/2012 | Noland et al. |
| 2014/0091254 | A1 | 4/2014 | Noland et al. |
| 2016/0023921 | A1 | 1/2016 | Addiego et al. |

FOREIGN PATENT DOCUMENTS

| | | |
|---|---|---|
| CN | 105170644 A | 12/2015 |
| EP | 0646642 A2 | 5/1995 |
| EP | 0962492 B1 | 1/2005 |

OTHER PUBLICATIONS

Tiehm, A., et al., Biological Activated Carbon Barriers for the Removal of Chloroorganics/BTEX Mixtures; Activated Carbon and Other Support Media Used for Biobarriers, Sixth International In Situ and On Site Bioremediation Symposium; San Diego, CA, Jun. 7, 2001., p. 105-112.

Communication pursuant to Rule 114(2) EPC; for the Examining Division; Applicant Remediation Products, Inc., Appl. No. 03764339.2-2104/1521723; Dated Mar. 29, 2010, European Patent Office.

Jones, Valiant K., et al., Effects of Crystallite Size and Support on the CO Hydrogenation Activity/Selectivity Properties of Fe/Carbon; Journal Phys. Chem., 1986, 90, 4832-4839.

Leng, C. C., et al., "Effects of Surface Properties of Activated Carbons on Adsorption Behavior of Selected Aromatics," Carbon vol. 35, No. 9, 1997, pp. 1375-1385.

Martin-Martinez, Jose M., et al., "Carbon-Supported Iron Catalysts: Influence of Support Porosity and Preparation techniques on Crystallite Size and Catalytic Behavior," Ind. Eng. Chem. Res. 1991, 30, 2263-2275.

Wang, Chuan-Bao, et al., "Synthesizing Nonoscale Iron Particles for Rapid and Complete Dechlorination of TCE and PCBs," Environmental Science & Technology, vol. 31, No. 7, 1997, 2154-2156.

Elliott, Daniel W., et al., "Field Assessment of Nanoscale Bimetallic Particles for Groundwater Treatment," Environmental Science & Technology, vol. 35, No. 24, 2001, 4922-4926.

Ponder, Sherman M., et al., "Surface chemistry and Electrochemistry of Supported Zerovalent Iron Nanoparticles in the Remediation of Aqueous Metal Contaminants," Chemical Mater. 2001, 13, 479-486.

Pinna, Francesco, "Supported Metal Catalysts Preparation," Catalysis Today 41 (1998) 129-137.

Hegenberger, E., et al., "Evidence of Strong Interaction betwen Iron Particles and an Activated Carbon Support," Jounal Phys. Chem., 1987, 91, 5067-5071.

Oliveira, et al., Activated Carbon/iron oxide magnetic Composites for the adsorption of contaminats in water. Carbon 40 (2002) 2177-2183.

Muftikian et al., A method for the rapid dechlorination of low molecular weight chlorinated hydrocarbons in water. Wat. Res. Vol. 29. No. 10 (1995) 2434-2439.

*Remediation Products, Inc.*, v. *Adventus Americas, Inc., et al.*, "Adventus Americas, Inc. and Environmental Technologies, Inc., Opposition to Plaintiff's Motion for Partial Summary Judgment," in the United States District Court for the Western District of North Carolina, Charlotte Division, Civil Action No. 3:07CV00153, filed May 19, 2008.

*Remediation Products, Inc.*, v. *Adventus Americas, Inc., et al.*, In the U.S.D.C. Western District of NC, Civil Action No. 3:07CV00153, Memorandum in Opposition to Plaintiff's Motion for Partial Summary Judgment on U.S. Pat. No. 5,534,154, Document 162, Filed Jul. 2, 2009.

Millerick, et al, Electron Shuttle-Mediated Biotransformation of Hexahydro-1,3,5-trinitro-1,3,5-triazine Adsorbed to Granular Activated Carbon, Environ. Sci. Technol. 2013, 47, 8743-8750.

Stevenson, et al, "Changes in Structure and Properties of Starch of Four Botanical Sources Dispersed in the Ionic Liquid, 1-butyl-3-methylimidazolium Chloride," Carb. Polymers, 67:21-31 (2007).

Tamara, et al., "Effects of Iron Purity and Groundwater Characteristics on Rates and Products in the Degradation of Carbon Tetrachloride by Iron Metal," Environ. Sci. Techno., 38:1866-1876 (2004).

Baqai, et al., "Isolation and Screening of Enzymatic Hydrolysis of Starch by Enzyme Amylase from Soil Isolate Aspergilllus Niger," Rads J. Biol. Res. App. Sci., 6(1):29-34 (2015).

COMPOSITION WITH A TIME RELEASE MATERIAL FOR REMOVING HALOGENATED HYDROCARBONS FROM CONTAMINATED ENVIRONMENTS

CROSS-REFERENCE TO RELATED APPLICATIONS

This application is a divisional of U.S. patent application Ser. No. 16/686,561, filed Nov. 18, 2019, which is a continuation-in-part of U.S. patent application Ser. No. 15/147,733, filed May 5, 2016, both of which are incorporated herein in their entireties.

BACKGROUND OF THE DESCRIPTION

1. Field of the Description

The present invention relates to compositions and methods for in situ remediation of contaminated environments, and particularly to the remediation of soil and/or groundwater contaminated with halogenated hydrocarbons.

2. Description of the Related Art

With increased concerns over protecting the environment and public health and safety, the identification and removal of contaminant materials in the environment, and especially from the groundwater supply, has become one of the most important environmental concerns today. Years of unregulated dumping of hazardous materials have severely contaminated the groundwater in many areas, creating significant health concerns and causing extensive damage to the local ecosystem. As a result, in recent years significant emphasis has been placed upon the clean-up and remediation of contaminated groundwater and the environment surrounding dump sites, which has led to the creation of a new industry of environmental clean-up and remediation. However, conventional technologies currently being used for remediation for contaminated sites often are very expensive, can require years to perform, and are not always effective.

Because of the widespread use of both chlorinated solvents and petroleum hydrocarbons, contaminated ground water has been found in many sites around the world. Chlorinated solvents, such as trichloroethane (TCE) and perchloroethylene (PCE), are used for such purposes as dry cleaning, and as degreasers and cleaners in a variety of industries. Petroleum hydrocarbons commonly found in ground water include the components of gasoline, such as benzene, toluene, ethylbenzene, and xylene. Another common contaminant of ground water is naphthalene. Additional groundwater and soil contaminants include polycyclic aromatic hydrocarbons (PAHs) created from combustion, coal coking, petroleum refining and wood-treating operations; and polychlorinated biphenyls (PCBs), once widely used in electrical transformers and capacitors and for a variety of other industrial purposes, pesticides, and herbicides.

Various ex situ and in situ methods have been utilized for the treatment, remediation, and disposal of contaminated soil. Ex situ methods generally include permanent removal of the contaminated soil to a secure landfill, incineration, indirect thermal treatment, aeration, and venting. Removal of contaminated soil to landfills is no longer an attractive alternative because of the high excavation, transportation, and disposal costs and because of the potential for residual liability. Incineration and indirect thermal treatment can be achieved either on-site or off-site but, in either case, involves excavation, handling, and treatment of substantially all the contaminated soil as well as significant amounts of soil adjacent to the contaminated soil. The soil must then either be transported to the treatment facility or else the treatment apparatus must be installed on-site. Other elaborate and expensive techniques that have been utilized involve excavation and treatment of the contaminated soil using multi-step unit operations for separating and recovering the soil from the contaminants.

Additional existing clean-up methods and technologies include "pump and treat" methods in which contaminated groundwater is pumped to the surface, cleaned chemically or by passing the groundwater through a bioreactor, and then reinjected into the groundwater. Such a process generally is carried out over a long period of time, typically one to ten years or more. A common remediation treatment for ground water contaminated with chlorinated hydrocarbons involves pumping the water out of the well or aquifer, volatizing the contaminants in an air stripping tower, and returning the decontaminated water to the ground site. A related type of environmental remediation is the "dig and haul" method in which contaminated soils are removed and then treated or land filled.

The biggest problem with pump and treat systems is that, over time, they become more and more inefficient, so that stable residual concentrations become established. When this happens, the system is said to be "flat-lined" and very little further benefit is obtained. In addition, channeling often occurs so that large pockets of contamination are left behind, and rebound frequently occurs after the pumps are turned off.

A wide variety of materials and methods have been evaluated for in situ remediation of chlorinated hydrocarbons, including zero valent iron (ZVI), potassium permanganate, and hydrogen peroxide. ZVI renders the chlorinated hydrocarbon less toxic by reductive dehalogenation, i.e., by replacement of chlorine substituents with hydrogen. In this method, reactive walls are constructed by digging a trench across the plume migration path and filling it with iron filings. Sheet piling or some other means of directing the flow of groundwater is used to direct contaminated groundwater through the filing wall. The chlorinated hydrocarbons react with the elemental iron as the groundwater flows through the wall, and ideally, clean water emerges on the down gradient side of the wall. The disadvantage of the wall method lies in the difficulty of introducing large volumes of solid reactive material, such as iron particles, at effective depths. Conventional excavation methods generally limit the practical working depth to about 30 feet, whereas ground water contaminants are found at depths as great as 300 feet. Also, there may be a reduced permeability in the wall over time due to precipitation and plugging. Further, the reactive wall approach may not be useful in degrading methylene chloride and may be very slow (e.g., taking up to 10 or more years to achieve any substantial remediation).

Oxygen release materials (ORMs) are compositions such as intercalated magnesium peroxide that release oxygen slowly and facilitate the aerobic degradation of hydrocarbon contaminants in situ. ORMs are most effective when used to polish up after a mechanical system has flat-lined and are least effective at new sites where no other remedial measures had been implemented. They are disadvantaged in that ORMs are expensive, and large amounts are required for complete oxidation. Additionally, multiple treatments are often required in order to achieve targeted cleanup goals, and up to five years may be needed to complete the process.

Hydrogen Release Compound® (HRC) is an alternative option for the in situ remediation of chlorinated hydrocarbons under anaerobic conditions via reductive dehalogenation. When in contact with subsurface moisture, HRC® is hydrolyzed, slowly releasing lactic acid. Indigenous anaerobic microbes (such as acetogens) metabolize the lactic acid producing consistent low concentrations of dissolved hydrogen. The resulting hydrogen is then used by other subsurface microbes (reductive dehalogenators) to strip the solvent molecules of their chlorine atoms and allow for further biological degradation. HRC® is injected into the affected environment under pressure and each treatment lasts for roughly six to nine months. Like ORMs, HRC® is expensive, and large amounts are required for complete degradation. Additionally, multiple treatments are always required in order to achieve targeted cleanup goals, and up to five years may be needed to complete the process.

Another emerging clean-up technology is "bioremediation," in which natural or genetically engineered microorganisms are applied to contaminated sites such as groundwater, soils or rocks. In this technique, specialized strains of bacteria are developed that metabolize various hydrocarbons such as gasoline, crude oil, or other hydrocarbon-based contaminates and gradually reduce them to carbon dioxide and water. However, such bacterial remediation requires that the bacteria and the hydrocarbon be brought into intimate contact under conditions in which the bacteria will act to metabolize the hydrocarbons. This requires extensive labor and effort to spread the bacteria on the soil and then to continually work and rework the contaminated area, turning and tilling the soil, until such time as the bacteria have been brought substantially into contact with all the contaminated hydrocarbon particles. An additional drawback has been the ineffective spreading of injected bacteria due to clogging around the wells due to adsorption and growth of the bacteria about the wells.

The above-described technologies share one or more of the following drawbacks: (1) long periods of time are required for sustained reduction in contaminant concentrations to be realized; (2) although reductions can be realized, regulatory cleanup standards or goals for soil and groundwater are seldom attained; (3) performance is inconsistent and highly dependent on site conditions and contaminant levels; (4) with respect to active systems, contaminants are often removed from one formation (groundwater for example) and then released into another, such as air, and as a result, contaminants are not destroyed, just moved from one place to another; and (5) with respect to passive systems for treatment of chlorinated solvents, by-products are often released that are more toxic than the original contaminants, creating a transient condition more egregious than what existed before treatment.

Hence, a need remains for remediation processes to effectively clean up soil and/or groundwater contaminated with hydrocarbons and/or halogenated hydrocarbons that is rapid, cost effective, and does not release toxic by-products into the soil, air or groundwater.

SUMMARY

The present description provides compositions and methods for in situ soil and/or groundwater remediation that can reduce contaminant concentrations quickly to regulatory cleanup standards. The compositions and methods work in a variety of soil and groundwater conditions and are applicable for the remediation of a variety of contaminants. The methods and compositions of this description do not release toxic by-products into the soil, groundwater, or air and have no impact on soil properties or groundwater quality. The compositions of this description are also cost effective in that they remain active for an extended period of time so that only a single treatment is required.

In prior work, the inventor created a composition which, when added to a site such as soil and/or groundwater contaminated with one or more halogenated hydrocarbons, adsorbs the halogenated hydrocarbons, and reduces them to less innocuous by-products. This composition was a granular activated carbon whose inner pore structure had been impregnated with elemental iron. This elemental iron-based composition may be considered a supported reactant for in situ remediation of soil and/or groundwater contaminated with one or more halogenated hydrocarbon. The supported reactant was formed mainly of an adsorbent impregnated with zero valent iron, and the adsorbent is chosen to be capable of adsorbing the halogenated hydrocarbon contaminants as well as the intermediate by-products resulting from the degradation of the contaminants. In one embodiment, the adsorbent is activated carbon. The inventor determined that this elemental iron-based composition was useful in methods for the remediation of an environment contaminated with halogenated hydrocarbons, with such methods including adding the supported reactant to one or more sites of the contaminated environment. In this manner, reductive dehalogenation of the halogenated hydrocarbon contaminants is achieved.

Regarding the present description, though, the inventor further recognized there may be a useful synergy between this elemental iron-based composition and bioremediation technologies. Particularly, it was understood that successful degradation of halogenated hydrocarbons or other contaminants is often mainly about achieving successful electron transfer. To this end, the elemental iron-based composition may be used with a first blend of organisms that are chosen for their ability to degrade chlorinated solvents and other halogenated compounds. For example, the elemental iron-based composition may act to absorb the contaminants within the pores of the activated carbon near the impregnated iron, which acts in conjunction with this first blend of organisms to degrade the contaminants.

Further, though, the inventor recognized that it is desirable to "feed" or "fuel" the organisms of the first blend/composition to continue to degrade the contaminants over a longer period of time. Prior substrates used for this purpose often were ineffective as they donate hydrogen or the like very quickly and do not continue to be effective in feeding or fueling the first blend of organisms over time (e.g., over 20 to 40 days or more).

To this end, the inventor discovered that it would be useful to provide a combination of an organic compound (or polymeric substance or polymer) such as a complex carbohydrate to fuel/feed the first blend of organisms and a second blend of organisms whose sole purpose/function is to break the organic compound(s) into smaller molecules that are more readily utilized by the microorganisms of the first blend to support degradation of the contaminants. In this way, the fuel or smaller molecules from the substrate are made available in a time released manner (e.g., the organic compound with the organisms acts as a time release material) that facilitates the degradation of the contaminants over a much longer period of time so as to achieve greater percentages of degradation (e.g., 64 to 86 percent degradation achieved in some bench trials). In particular implementations, the organic compound is a complex carbohydrate that is (or includes) starch (such as a food grade starch from a source such as corn, starch, rice, wheat, or the like) while other exemplary, but not limiting, implementations utilize chitin.

More particularly, a composition is provided that is particularly well suited for remediation of soil, wastewater, or groundwater containing halogenated compounds (such as halogenated fuels, chlorinated solvents, and the like). The remediation composition includes an elemental iron-based composition, and a first bioremediation material including at least one microorganism (and typically a blend of many microorganisms such as unicellular organisms or bugs such as bacteria, archaea, and the like and also including fungi and other organisms as taught herein) capable of degrading halogenated compounds. Significantly, the remediation composition further includes an organic compound or polymeric substance (or polymer) such as a polysaccharide (e.g., a complex carbohydrate (such as a food grade starch)) and a second bioremediation material including at least one organism (and typically a blend of many microorganisms) capable of degrading the complex carbohydrate. The remediation composition is a "time release material" because degrading of the organic compound or polymeric substance (e.g., a complex carbohydrate such as starch, chitin, or the like) by the organisms of the second bioremediation material is performed over a time period of at least 20 days such as 365 or more days (e.g., the time release functionality may extend over one to three or more years in some cases).

In some useful embodiments, the organic compound includes a complex carbohydrate in the form of a starch (e.g., a food grade starch such as corn, wheat, rice, tapioca, potato (including sweet potato), sago, mung bean, or arrowroot starch or a blend of such starches) while other remediation compositions utilize chitin. In practice, degrading of the organic compound or polymeric substance by the at least one organism of the second bioremediation material comprises breaking the organic compound into a plurality of smaller molecules utilized (e.g., as electron donors) by the at least one organism of the first bioremediation material during the degrading of the halogenated compounds.

The remediation composition may be effectively implemented in one embodiment when the elemental iron-based composition includes activated carbon with pores impregnated with zero valent iron (ZVI). In the same or other implementations, the elemental iron-based composition may include activated carbon that is capable of adsorbing the halogenated compounds and that has numerous pores impregnated with iron. In some preferred embodiments, the iron (or elemental iron particles) is impregnated into the activated carbon by being at least partially dissolved into walls of the pores, and transitions between the activated carbon and the iron include cast iron and iron carbide, which may make the elemental iron-based composition much more effective at degrading halogenated compounds.

In some embodiments, the elemental iron-based composition has between about 1 and 20 percent by weight of the iron. In these or other embodiments, the exposed surface area of the iron is between about 50 and 400 m$^2$/g. Further, it may be desirable for the activated carbon to have a surface area between about 800 and 2000 m$^2$/g.

DETAILED DESCRIPTION

The following description relates to new remediation compositions and methods for in situ remediation of environments such as soil or groundwater contaminated with halogenated hydrocarbons. The description builds upon prior discoveries made by the inventor of a supported reactant (or elemental iron-based composition) that is particularly well suited for cleaning up soil and groundwater contaminated with halogenated hydrocarbons. The effectiveness of this supported reactant/elemental iron-based composition is greatly enhanced, though, by combining it with bioremediation technologies (e.g., a set or blend of one-to-many microorganisms) suited for degrading halogenated hydrocarbons to create a new remediation composition.

Further, the effectiveness of the bioremediation technologies is increased by including in the new remediation composition a combination of a time release material (or organic compound or polymeric substance (such as a complex carbohydrate (e.g., starch, chitin, or the like)) with a second set or blend of one or more microorganisms chosen for breaking up or degrading the time release material (e.g., a complex carbohydrate) into smaller molecules for better utilization over time by the second set or blend of microorganisms. Stated differently, the elemental iron-based composition (or supported reactant as called herein) combined with the organic compound(s) or polymeric substance(s) (e.g., a starch (or other complex carbohydrate) and microorganisms degrading organic compounds/polymeric substances provide a time release composition or platform that acts to enhance and support (e.g., fuel) the degradation over a relatively long period (e.g., 20 to 365 days or more). This time release platform is used (as it slowly releases hydrogen or the like) in the new composition described herein by the set or blend of microorganisms included that degrade the contaminants such as halogenated hydrocarbons.

With regard to "the time release material" to be used, the inventor understood that polymers are large molecules formed when monomers link together to form the larger molecule. The monomer can be a simple compound like ethylene (CH$_2$CH$_2$) or a more complex substance or material such as a sugar. In general, polymers have the following structure: [repeating unit]n, where the repeating unit is a monomer and n is the degree of polymerization. With respect to degradation of halogenated organic compounds, many simple substances have been used to promote such degradation. However, they are typically very short lived and include sugars and fatty acids like lactic acid. As previously described, these simple substances or compounds are water soluble and readily consumed by a variety of microorganisms.

Hence, the inventor recognized the need for a time release material that would be a source of such compounds that play the role of a substrate that can be beneficially used by organisms capable of degrading halogenated compounds. Specifically, the inventor discovered that organic compounds or polymeric substances (or polymers) were good sources of such time released materials. Naturally occurring polymers may be preferred in some applications, but man-made polymers may also be used to practice remediation products/processes of the present description.

Naturally occurring polymers fall into three general types or categories: (1) polynucleotides; (2) polyamides; and (3) polysaccharides. Of these, the inventor discovered that polyamides and polysaccharides are likely the most applicable and useful. In some specific embodiments, one of the more effective polymeric substances or organic compounds presented in this description are complex carbohydrates such as one or more starches (which are polysaccharides). Polymers contain monomeric units that can fulfill the role of a time release material, which is beneficially used to support degradation of halogenated compounds. Polymeric fatty acids such as polylactic acid and polymers of amino acids (polyamides) are additional examples of organic compounds or polymeric substances that may be utilized. Short chains of amino acids with 6 to 30 acids linked together by peptide bonds are referred to as polypeptides. When the number of amino acids reaches 40 or more (molecular weight of 5000 Da (Daltons)), the chain takes on the properties associated with proteins. Examples of proteins that may be used in the remediation compositions include casein, yeast extract, and peptone.

In general, polymeric substances that can be used as part of the remediation compositions described and claimed herein include organic compounds, which typically will include monomeric units that can be used as a time release material supporting the degradation of halogenated organic compounds with average molecular weight exceeding 2500 Da or more preferably exceeding 5000 Da. Polysaccharides may alternatively be characterized according to the general formula $C_x(H_2O)_y$, where x is an integer greater than 12 and preferably where x is an integer between 200 and 2500 and further where x and y are different integers. Alternatively, polysaccharides may be characterized according to the general formula $(C_6H_{10}O_5)_n$, where n is an integer that, in one embodiment, is greater than or equal to 40 and less than or equal to 3000.

The following description provides specific examples of polymeric substances and/or organic compounds in the form of complex carbohydrates such as food grade starch. However, it will be understood by those skilled in the art that these are non-limiting examples and other organic compounds or polymeric substances may be substituted in these remediation compositions. The description also discusses the supported reactant or elemental iron-based composition that is included in the new remediation composition and how it may be manufactured. The description provides a method of using the new remediation composition to decontaminate soil and/or groundwater. The description then proceeds to detail possible mixtures or "recipes" for providing or manufacturing the new remediation composition.

More specifically, the remediation composition may include a supported reactant for the reductive dehalogenation of halogenated hydrocarbons. The reactant may consist essentially of an adsorbent impregnated with zero valent iron, and the adsorbent may have an affinity for halogenated hydrocarbons. In addition, the adsorbent can be chosen so as to be capable of adsorbing toxic intermediate by-products produced by the reductive dehalogenation of the contaminants, e.g., intermediates such as dichloroethane and intermediate by-products of trichloroethane decomposition. In this way, the adsorbent provides a means for concentrating contaminants into a new matrix where a high surface area of iron is available, as discussed hereinafter in detail. The supported reactants accomplish treatment of halogenated hydrocarbons in soil and groundwater, at least in part, by degrading halogenated hydrocarbon contaminants and their toxic intermediate by-products into harmless by-products (e.g., ethane, ethene, etc.).

The supported reactants are in some implementations prepared using an adsorbent having a high surface area per unit weight and a high affinity for halogenated hydrocarbons. Suitable adsorbents for these purposes include, but are not limited to, activated carbon, vermiculite, alumina, zeolites, and chars such as wood, bone, and the like. Thus, while the method of preparing the supported reactants is described utilizing activated carbon as the adsorbent, it is to be understood that the methods and supported reactants that may be used in the new remediation composition are not limited to only this adsorbent.

In one non-limiting embodiment, the supported reactant consists essentially of activated carbon as the support, and the activated carbon is impregnated with zero valent iron. The activated carbon preferably has a high surface area per unit weight (preferably ranging from 800 to 2000 $m^2/g$) and a high affinity for halogenated hydrocarbons. The ability of activated carbon to adsorb organics from water enhances its utility as a support. However, while the activated carbon can trap hydrocarbon contaminants, carbon by itself is not stable over long periods, i.e., it is subject to erosion, in which case the contaminants move with the activated carbon and are not truly trapped and removed. Activated carbon provides an efficient matrix for adsorption of the chlorinated hydrocarbon contaminants. Impregnating the activated carbon with the zero valent iron provides sub-micron deposits of iron within the pore structure of the carbon, thus maximizing the metal's available surface area and placing the metal where the concentration of adsorbed contaminant molecules is the highest. Accordingly, the supported reactant allows efficient contact of the iron with adsorbed chemicals contaminants, since the iron will be in close proximity to the contaminant. The supported reactants of the new remediation composition accomplish treatment of chlorinated hydrocarbons in soil and groundwater by degrading these chemicals into harmless by-products.

Activated carbons can be manufactured from a broad spectrum of material including, but not limited to, coal, coconut shells, peat, and wood. The raw material is typically crushed, screened, and washed to remove mineral constituents. The material is then activated at high temperatures (typically over 900° C.) in a controlled atmosphere to produce a material having an extensive porous network and a large surface area (e.g., ranging from 1000 to 2000 $m^2/g$). The supported reactants may be produced with virtually any source of activated carbon. All that is needed are minor adjustments in system design parameters to account for the different forms of carbon. When the product is used for remediation of groundwater, acid-washed carbons may be useful since the acid wash removes any extraneous metals that may be of environmental concern from the carbon.

With activated carbon, available surface areas for adsorption preferably range from about 800 $m^2/gm$ to 2000 $m^2/gm$. Some loss of carbon surface area may occur during the impregnation process, but testing has shown that the loss is not significant when measured by adsorption isotherms. In one embodiment, the surface area of the zero valent iron used in the supported reactant included in the remediation composition ranges from about 50 to 400 $m^2/(gm$-deposited iron). The weight percent of iron deposited within the carbon matrix ranges from about 1 percent to 20 percent by weight of iron and, in some useful embodiments, in the range of about 7 to 8 percent by weight of iron. In one embodiment, the supported reactant has a total surface area of over 1500 $m^2/g$. The iron contained in the supported reactants typically is a high purity iron. In other words, the iron does not contain other metals, such as heavy metals, which would contaminate groundwater and drinking water beyond limits allowed by the EPA. Preferably, the iron is at least 99% pure, and the concentrations of trace contaminants such as chromium, aluminum, potassium, cesium, zinc, lead, nickel, cadmium, and/or arsenic are less than 5 ppm. In some cases, the source of the iron is a food grade salt.

In one particular embodiment, a supported reactant used in the remediation composition for in situ remediation of soil and/or groundwater contaminated with a halogenated hydrocarbon, includes (or even consists essentially of in some cases): (i) an adsorbent impregnated with zero valent iron and (ii) a metal hydroxide or a metal carbonate (such as limestone) in an amount sufficient to provide a reactant having a pH greater than 7. The adsorbent is selected to be capable of adsorbing the halogenated hydrocarbon. Suitable adsorbents for purposes of this invention include, but are not limited to, activated carbon, vermiculite, alumina, and zeolites.

As described above, the contaminants in the soil/ground water being remediated are initially adsorbed by the activated carbon and then degraded through a reductive dechlorination mechanism. However, toxic reaction by-products such as vinyl chloride and cis-dichloroethene may be formed during the treatment process. In conventional remediation systems, even though these by-products will react with the iron, they do so at a reduced rate and concentrations can initially rise. In fact, fairly large accumulations can occur, creating a more acute risk to the environment than that which originally existed. One of the advantages of the supported reactant described herein for use in the remediation composition is that these toxic by-products are also readily adsorbed by the activated carbon. As a result, little if any by-product escapes from the carbon matrix and groundwater quality is protected throughout the cleanup lifecycle. Further, the supported reactant degrades the intermediate by-products into non-toxic by-products such as ethane, ethene, and ethyne.

Manufacture of the supported reactant may involve methods that produce an adsorbent (e.g., activated carbon) impregnated with zero valent iron, which can be achieved using a variety of procedures known to those skilled in the art. A first exemplary method of producing a supported reactant involves mixing the adsorbent with a calculated amount of a hydrated iron salt such as ferric nitrate while warming to melt the hydrated iron salt. The iron can be an iron (II) or an iron (III) salt. The mixture is dried and pyrolyzed to decompose the iron salt to iron oxide, forming an intermediate product (i.e., the activated carbon impregnated with a form of iron oxide). The intermediate product is then subjected to reduction conditions to reduce the iron oxide to elemental iron, thereby producing the activated carbon impregnated with elemental iron.

A second exemplary method for preparing a supported reactant involves a slow precipitation of goethite (iron hydrogen oxide) from a solution of an iron salt (e.g., ferrous sulfate) by addition of a dilute sodium bicarbonate solution. The precipitation is carried out with vigorous mixing in a suspension of the activated carbon to provide an intermediate product (i.e., the adsorbent impregnated with a form of iron oxide). This intermediate product is then washed, dried, and finally reduced to convert the iron oxides to elemental iron, thereby producing the activated carbon impregnated with elemental iron.

A third exemplary method of preparing a supported reactant involves treatment of the activated carbon with a solution of a water soluble iron salt, such as iron (II/III) sulfate, iron chloride, iron citrate, iron nitrate, or any other suitable water soluble iron salt. The solution can be sprayed onto the carbon or the carbon may be suspended in a measured volume of the iron salt solution sufficient to achieve the desired loading. The suspension is then de-aerated by applied vacuum. Depending on the chosen process for final reduction, the salt impregnated material can be dried and reduced directly, or neutralization of the salt may be provided by the addition of a dilute sodium bicarbonate or sodium hydroxide solution over a period of time, thereby producing iron oxides/hydroxide within the carbon. In the latter case, the iron oxide or iron hydroxide-impregnated activated carbon is then subjected to reducing conditions to reduce the iron oxide or iron hydroxide to zero-valent iron.

In one embodiment, the effectiveness of the supported reactant is enhanced by increasing the pH of the supported reactant to a basic pH, such as by adding a small percentage of magnesium hydroxide (or other metal hydroxide or, in some cases, a metal carbonate (such as limestone)) to the supported reactant to raise the pH above 7.0.

The remediation composition that includes these supported reactants (along with blend or set of one or more organisms for bioremediation, a complex carbohydrate, and a blend or set of organisms for degrading the complex carbohydrate) can be applied to treatment of water contaminated with a variety of water miscible or soluble halogenated organic compounds. Chlorinated solvents are particularly common contaminants in aquifers and other subsurface water-containing environments. Contaminants that may be effectively treated include halogenated solvents such as, but not limited to, (TCE), dichloroethylene (DCE), tetrachloroethylene, dichloroethane, vinyl chloride (VC), chloroethane, carbon tetrachloride, chloroform, dichloromethane and methyl chloride. Other classes of contaminants that may be effectively treated include brominated methanes, brominated ethanes, brominated ethenes, fluorochloromethanes, fluorochloroethanes, fluorochloroethenes, polychlorinated biphenyls (PCBs), and pesticides.

In this regard, the description provides a method of remediating a site contaminated with halogenated hydrocarbons. The method includes injecting a remediation composition with a supported reactant of this description into one or more locations of the contaminated site. Illustrative examples of contaminated environments that can be treated with the remediation composition with a supported reactant combined with bioremediation organisms (and a starch or other complex carbohydrate and degrading organisms) include, but are not limited to, soil, sediment, sand, gravel, groundwater, aquifer material, and landfills. For example, in one embodiment, the remediation composition with supported reactant is injected into multiple sites within an aquifer, as described in Example 3. In this embodiment, the application method results in a substantially homogeneous distribution of the remediation composition with supported reactant in the contaminant plume, as opposed to creating a barrier or filled trench as in conventional methods. Thus, the remediation method according to the embodiment described in Example 3 using a remediation composition with supported reactant does not rely on groundwater advection for effective treatment. Rather, the activated carbon component of the supported reactant of the remediation composition concentrates the contaminants within the adsorbent matrix where a high surface area of iron is available, thereby increasing the rate of contaminant degradation. Contaminated ground water in the site subsequently contacts the supported reactant, whereby reductive dehalogenation of the halogenated hydrocarbon compounds is achieved in combination with the blend or set of organisms included for degrading halogenated compounds.

The supported reactant provides a number of advantages over conventional remediation products and methods. For example, it rapidly reduces concentrations of contaminants in groundwater so that regulatory standards can be approached or achieved in a short time frame (e.g., within several days or a few weeks, versus several months or years with conventional methods). In addition, the supported reactant is non-toxic, does not decompose over time, and toxic degradation by-products are not released, so groundwater quality is protected throughout treatment. The supported reactant has the ability to treat a variety of chlorinated chemicals and is effective in all types of soil and groundwater conditions. It remains active for an extended period of time so that typically only a single treatment is required. This "time release" characteristic is effectively paired with the time release characteristics of the complex carbohydrate and blend or set of microorganisms provided in the remediation composition to degrade or break up the complex carbohydrate into smaller molecules to be utilized more effectively and over time (e.g., 20 to 365 days or more) by the blend or set of organisms provided for assisting the supported reactant in degrading the halogenated hydrocarbons. Further, the material is easy to use and does not require any special safety controls or equipment for installation.

The remediation composition and its use in remediating contaminated soil/groundwater is further illustrated by the following non-limiting examples. All scientific and technical terms have the meanings as understood by one with ordinary skill in the art. The specific examples which follow illustrate the methods in which the compositions of the present description may be prepared and are not to be construed as limiting the invention in sphere or scope. The methods may be adapted to variation in order to produce compositions embraced by this description but not specifically disclosed. Further, variations of the methods to produce and use the same compositions in somewhat different fashion will be evident to one skilled in the art.

EXAMPLE 1

Preparation of a Supported Reactant by Low Temperature Decomposition of Metal Nitrates A measured amount of activated carbon is mixed with an associated amount of hydrated ferric nitrate calculated to provide the desired weight percentage of elemental iron in the final product, e.g., 1 to 20 percent by weight iron. The iron salt is typically moist and on warming easily melts, so that a uniform mixture results. As the mixture is stirred, it is warmed to roughly 50° C. to melt the salt. If necessary, a small amount of water may be added to produce a mixture having a creamy consistency. The mixture is then dried at a temperature of from 90 to 110° C. so that the mixture can be crushed to a free flowing granular powder. Some decomposition of the nitrate salt occurs during this process.

The dried powder is then loaded into a furnace and heated in accordance with a temperature program while maintaining reducing conditions throughout. Initially, the temperature is slowly raised to 150 to 200° C. to completely dry the reactant and continue degradation of the iron nitrate. The temperature continues to increase, and, at 300° C., the nitrate salt is completely decomposed into oxide.

Once the nitrate is completely degraded into oxide, a reducing gas such as methane gas or hydrogen gas is introduced into the furnace atmosphere and the temperature is raised to from 550 to 850° C., completely reducing the oxide to elemental iron. Note, the temperatures often are significant as the inventor has found that if the temperature is too low as the iron is formed the iron does not dissolve into the carbon, and, as a result of this failure to dissolve into the carbon, one of the most important features of the iron impregnated carbon may not be realized. Methane gas is safer to use than hydrogen and, therefore, is preferred in some implementations. The theoretical amount of water is typically formed upon complete reduction of the oxide as the temperature rises to between 400 and 450° C. when 100% hydrogen or methane is used.

Final properties of the supported reactant are influenced by the ultimate reducing temperature. For example, when the reactant is reduced at temperatures below 700° C. and then exposed to the air after cooling, an exothermic reaction may occur, oxidizing a portion of the reduced iron. However, when the final reduction is carried out at a high temperature, for example between about 700 and 850° C., the reactant is stable and exposure to the air has no effect. If reduction is completed at a temperature of less than 450° C., the material can be pyrophoric. At reduction temperatures between about 450 and 700° C., various reactant activities can be obtained.

EXAMPLE 2

Preparation of a Supported Reactant by a Precipitation Procedure

An appropriate amount of hydrated iron sulfate is dissolved in deionized water in a tank with stirring, and a measured amount of activated carbon is added. Stirring is continued after the addition is complete, and a vacuum is applied to the tank to de-aerate the carbon. Once the carbon is de-aerated, a sufficient amount of a dilute solution of sodium bicarbonate is slowly added to initiate precipitation of goethite and other iron oxides onto the suspended carbon. Pressurizing the tank during addition of the bicarbonate can enhance the impregnation process. After the addition of bicarbonate is completed, mixing is continued for several more hours. The process is complete when testing of an aliquot for ferrous iron is negative. The slurry is then washed with deionized water and filtered several times. Finally, the collected reactant is dried at 110° C. At this point, the carbon is impregnated with iron oxides and is ready for reduction.

The dried powder is loaded into a furnace and heated in accordance with a temperature program while maintaining reducing conditions throughout. Initially, the temperature is slowly raised to 150 to 200° C. to completely dry the reactant and continue degradation of the iron oxide and iron hydroxide. A reducing gas such as methane gas or hydrogen gas is introduced into the furnace atmosphere, and the temperature is raised to from 550 to 850° C., completely reducing the oxide to elemental iron. Again, it should be remembered that the higher reduction temperatures (e.g., 800 to 850° C.) have been proven by the inventor to provide the desired dissolving of the iron into the carbon, which is a highly useful feature of the impregnated carbon and may not be achieved at lower reduction temperatures. Methane gas is generally safer to use than hydrogen and therefore is preferred in some implementations. The theoretical amount of water is typically formed upon complete reduction of the oxide as the temperature rises to between 400 and 450° C. when 100% hydrogen or methane is used.

EXAMPLE 3

Application of a Composition to Remediate Soil/Groundwater

Small diameter (e.g., about 0.75 to 2 inches in diameter) injection rods are driven to targeted depths (e.g., 5-150 feet). The depth will depend on the power of the drill rig and the hardness of the soil. Hydraulically powered direct-push drill rigs are used to pound/push the injection rod to the desired depths, and then withdraw it about 6 inches to open up a small void below the injection point. A premixed aqueous suspension of a remediation composition with a supported reactant of this description is then injected under pressure down the rod. Pressure is allowed to build in the formation, and a slurry begins to flow out into the formation. No attempt is made to control the path of fluid flow, but, rather, the objective is to achieve a substantially homogeneous distribution of the suspension within the formation. The suspension tends to emanate outward in all directions from the base of the injection, and the average or effective radius of influence is controlled by the amount of fluid pumped into the rod.

After injection of the first batch of the suspension, a second (fresh) batch of the suspension can be prepared, a new injection rod installed, and the process repeated. Treatment in this fashion is continued throughout the plume, reducing concentrations of contaminants in the groundwater concentrations as treatment progresses. If one could view a cross-section of the formation, the treatment regime is intended to create a three-dimensional network of material, dispersed randomly and fairly uniformly throughout the treated formation.

Many treatment technologies, ZVI for example, only work well when installed in groundwater (saturated soils) and is not effective for treatment of vadose zone (unsaturated) soils. Because activated carbon is very effective at adsorbing organic compounds from vapor streams, the remediation compositions of this description are able to perform nearly as well when installed in the vadose zone. As a result, the remediation composition can be used equally well for treatment of contaminated soils and groundwater.

With this understanding of the elemental iron-based composition and the use of a remediation composition in mind, it may be appropriate at this point in the description to turn to formulas or recipes for the new remediation composition that builds upon the elemental iron-based composition (e.g., activated carbon with iron impregnated in its pores). Particularly, the inventor experimented with a variety of remediation compositions that include the elemental iron-based composition as part of the substrate for enhancing degradation of halogenated hydrocarbons by bioremediation compositions chosen for this specific purpose. This enhanced performance is achieved, it is believed, by a combination of capturing or absorbing the contaminants in the pores of the activated carbon near the elemental iron (e.g., zero valent iron particles) and then providing a hydrogen or electron source (or "fuel" source) for the bioremediation compositions that can be consumed over a longer period of time than prior substrates.

The new remediation composition can generally be thought of as including the following main ingredients or materials: (1) a first set or blend of one or more organisms (or a first bioremediation composition) that functions to degrade halogenated compounds (e.g., chlorinated solvents and the like); (2) an elemental iron-based composition (such as the supported reactant described above); (3) an organic compound or polymeric substance (such as one or more polyamides and/or polysaccharides (e.g., one or more complex carbohydrates); and (4) a second set or blend of one or more organisms (or a second bioremediation composition) that functions to degrade the organic compound or polymeric substance. Ingredients (2) to (4) may be considered a new composition or platform (or act together to form a new platform) to facilitate bioremediation functionality of the first set or blend of one-to-many organisms.

As background to the origin of the remediation composition, it is useful to understand that the inventor was considering the use of the elemental iron-based composition at sites contaminated with a broad mixture of contaminants. In one example (of many tests completed over years), the site's groundwater was known to contain alcohols, aromatics, ketones, chlorinated solvents, ethers, and aliphatic compounds. The challenge in remediating such a site is that no single known technology can address all the contaminants of concern. Testing of this exemplary showed that total contamination of the groundwater was roughly 2,000 ppm or 0.2% (wt) of toxic organic compounds.

As a consequence of this range of contaminants and the propensity for generation of recalcitrant daughter products, most remedial strategies (prior to the new remediation composition) would likely include the use of multiple techniques implemented in series over a period of time. Each technology in this series would be designed to target a very specific set of contaminants and would be used or run to its conclusion before the next technology targeting different contaminants would be employed at the site. With these issues in mind, the inventor discovered a combination of technologies (i.e., a new remediation composition as labeled herein) that would work together in a new and improved manner so as to provide one treatment that can be used on sites like the example provided above to achieve targeted cleanup levels. The use of just a single remediation composition is highly desirable—but not in existence prior to the new remediation composition—as it would provide a substantial reduction in time, cost, and the field effort. As will become clear, the discovered remediation compositions taught herein may be utilized (such as in the method discussed in Example 3) in the field to successfully remediate a contaminated site (e.g., a site with contaminants including halogenated compounds).

Trace metals were added to each test bottle of groundwater from the contaminated site along with the other ingredients of the remediation compositions. During an active remediation, though, there is typically no need to include trace metals to maintain good microbial growth as these are available from minerals in the subsurface and in groundwater. However, when only groundwater is utilized, some trace metals are needed. Also, micro and macro nutrients were added to the test vials or bottles to help create a very favorable environment for cell growth, but these nutrients typically are readily available in contaminated soils and groundwater and do not generally need to be included in a remediation composition.

With regard to useful and desirable ingredients for the new remediation composition, the first ingredient is a set or blend of one or more organisms chosen specifically to degrade the targeted contaminants. In this case, the targeted contaminants are halogenated compounds including chlorinated solvents and the like. The inventor used a remediation composition that included three differing sets or blends of such microorganisms, and the results showed that it is highly likely that a wide variety of sets/blends will be useful in remediation composition when combined with the other three ingredients in effectively degrading halogenated compounds. One set or blend of one or more microorganisms was commercially available (e.g., from vendors as a liquid concentrate) and was a blend of many organisms that in the past had been demonstrated to degrade fuel hydrocarbons such as benzene, toluene, xylenes, and the like. The second tested set or blend of microorganisms was a blend of organisms (again, commercially available as a liquid concentrate) that has proven (or is known) to be able to degrade chlorinated solvents and other halogenated compounds including chloroform cis-DCE (dichloroethylene), methylene chloride, TCE (trichloroethylene), VC (vinyl chloride), and chlorobenzene. The third tested set or blend of microorganisms was a blend of dehalococcoides (DHC) that is also commercially available (e.g., distributed by SiREM of Canada as KB-1®) and is designed to degrade various chlorinated compounds completely to hydrocarbon gases. Note, this first "ingredient" may include two or more vendor-provided compositions that are combined to degrade all the targeted contaminants of a particular site.

The second ingredient in the "recipe" for the bioremediation composition provided above is an elemental iron-based composition such as one including activated carbon and elemental iron. In some preferred embodiments, this elemental iron-based composition takes the form of one of the supported reactants described herein and which can be manufactured as described above so as to provide activated carbon with iron impregnated in its many pores. Such a supported reactant is effective for absorbing contaminants such as halogenated compounds within the pores near the elemental iron particles.

The third ingredient used in the making of the bioremediation composition is an organic compound or polymeric substance (such as a complex carbohydrate or other polysaccharide and/or a polyamide) while the fourth ingredient is a second set or blend of microorganisms, which is selected due to their ability to degrade the organic compound or polymeric substance (e.g., degrade particular complex carbohydrate such as a food grade starch). In one useful embodiment, this second set or blend of microorganisms in the tests was known to be able to degrade complex carbohydrates such as cellulose and starch to smaller compounds that can then be beneficially used by other organisms (e.g., those of the first set or blend in the remediation composition) to degrade site contaminants (e.g., halogenated compounds such as chlorinated solvents). When other organic compounds or polymeric substances are used, it may be desirable to choose the second set or blend of one or more microorganisms for its ability to degrade that organic compound(s) or polymeric substance(s). These two ingredients (or the elemental iron-based composition may also be included) may be thought of as providing a time release substrate for fueling degrading processes by the first set or blend of the microorganisms at a site.

In performing the bench tests, the inventor performed testing with a platform (or composition) in the form of lactic acid (in the form of sodium lactate but without a second blend of organisms used to degrade the lactate). Lactate is commonly used for bioremediation of chlorinated solvents in combination with blends of DHCs and other organisms effective at degradation of such compounds. These tests showed or verified that a significant limitation of lactate as a platform is that it is water soluble such that it tends to move with groundwater and is rapidly consumed such that it is ineffective for supporting degradation over longer periods of time (e.g., is not a "time release substrate"). As a result, in practice, remediation of sites with lactate as a platform require that a number of supplemental doses of lactate be applied to maintain a persistent concentration supportive of the degradation pathways. This undesirably adds to the cost and field work efforts of the remediation of a contaminated site.

In the bench tests, the inventor determined that it would be highly useful and desirable for the third and fourth ingredients of the remediation composition to be chosen to provide materials that could be beneficially used and consumed by the one or more microorganisms over an extended time period (e.g., 20 to 365 days or longer). Particularly, it was determined that organic compounds in the form of complex carbohydrates (e.g., food grade starch or chitin) are readily available and inexpensive and may provide the characteristics of a material useful in the substrate. It was recognized that, in contrast to lactate, many complex carbohydrates have low water solubility so that they are less likely to move with the groundwater than lactate. Further, the inventor recognized that the complex carbohydrates could be degraded or broken down over an extended period of time to provide a time release platform or composition for facilitating or supporting (during remediation processes) the first set or blend of organisms in the remediation composition.

Specifically, it was understood by the inventor that starch (e.g., a carbohydrate (or a polysaccharide) has a large number of glucose units joined by glycosidic bonds, and it may include two types of molecules in the form of linear and helical amylose and branched amylopectin, which may be provided in the form of food grade starch, may have low water solubility and may be easily degraded by a wide variety of organisms, which can be provided as the fourth ingredient of the remediation composition. Similarly, chitin (e.g., another natural polysaccharide) was identified by the inventor as another potential material for the remediation composition as it has low water solubility and has proven to be a useful platform or composition for degradation of chlorinated solvents using one or more microorganisms.

Both the starch and chitin were believed to have the potential to be "time release" sources of smaller molecules that can be utilized by the microorganisms (of the first set or blend) to more effectively perform degradation (e.g., degradation of chlorinated organic compounds (COCs) over time without a need for addition of more substrate materials). This potential was shown in the bench test in which starch or chitin (the third ingredient of the remediation composition) was used along with a second blend or set of one or more organisms chosen for their ability to degrade complex biopolymers (such as the complex carbohydrates of starch, chitin, and the like) to provide a time releasing mechanism for the smaller molecules/compounds used as "fuel" for degradation processes by the organisms of the first set or blend of one or more organisms in the remediation composition.

In the tests, the remediation composition was added to bottles of the ground water as follows: (1) 1.0 or 1.5 ml quantities of the first set or blend of one or more organisms (or more if two or more liquid concentrates from vendors was used to target different contaminants); (2) 1.5 or 2.0 grams nominal of the elemental iron-based composition; (3) 0.5 grams of the complex carbohydrate (e.g., starch, chitin, or the like); and (4) 1.0 or 1.5 ml quantities of the second set or blend of organisms. It is believed that the "starter" amount used for the first and second sets of organisms can be varied widely to practice the remediation composition as these will grow over time in use at a site. The ratio of the elemental iron-based composition to the complex carbohydrate may also be varied to provide a useful remediation composition with the given ratio of at least 1 to 2 being one useful example (e.g., with ratios of 1:1, 1:3, 1:4, and the like also considered within the breadth of this description). In brief, the bench testing verified that the remediation composition was effective over an extended period of time in degrading the halogenated compounds (e.g., in degrading the COCs to target levels).

In one implementation, the elemental iron-based composition used in the remediation composition was a granular activated carbon whose inner pore structure had been impregnated with elemental iron. The elemental iron-based composition was not simply a mixture of activated carbon and powdered iron, and it is inaccurate to even think of it as being activated carbon with bits of zero valent iron (ZVI) present within the pore structure. Instead, as discussed above, the manufacturing process for this key ingredient of the remediation composition may, in some preferred embodiments, begins with granular activated carbon (GAC) and impregnates this feedstock carbon with an aqueous solution of an iron salt. The intermediate product is then processed at higher temperatures (e.g., at or above 850° C.) under reducing conditions in a rotary furnace. Under these conditions, the iron salt decomposes, and elemental iron is formed. As it is formed, it partially dissolves into the carbon.

Significantly, the transition between the carbon and the metallic iron shows the presence of cast iron and iron carbide. This physical connection results in an interaction that activates the iron allowing it to perform in ways that ZVI and nano-scale iron powders alone cannot. One example of this is the ability of this elemental iron-based composition (or supported reactant) to degrade carbon tetrachloride and chloroform completely without generation of methylene chloride and also to degrade vinyl chloride. Further, this form of the elemental iron-based composition degrades halogenated compounds abiotically through chemical reduction.

With the above discussion in mind, it may now be useful to describe a number of useful aspects or characteristics of the supported catalyst (e.g., the elemental iron-based composition). The supported catalyst often will include coal-based activated carbon. Other materials can be used, but the final properties of the supported catalyst are highly dependent on the starting material. Bituminous coal-based carbons have been proven by the inventor to meet all adsorbent requirements detailed in this description. In one preferred embodiment, the carbon is activated in steam and carbon dioxide at approximately 1000° K for about 30 to 60 minutes. This supported catalyst has a carbon surface area in the range of 800 to 1800 $m^2/gm$. The activated carbon is capable of adsorption of halogenated organic compounds from vapor and liquid streams. The activated carbon is also preferably capable of adsorption of toxic intermediates arising from reaction of metallic iron with primary halogenated organic compounds (contaminants). The supported catalyst is fabricated or manufactured in many cases to have a metallic iron surface area in the range of 50 to 400 $m^2/gm$ iron. The loading of metallic iron is typically between 1 to 20% (wt). In practice, the metallic iron formed is preferably free of surface oxides or other coatings.

The reduction temperature used to produce the supported catalyst is 973 to 1200° K, with some embodiments using a reduction temperature of about 1140° K. This high temperature reduction is useful to develop the desired contact between the active carbon surface and the sub-micron deposits of metallic iron. It is also important in some applications to develop insensitivity to air exposure, which prevents creation of an oxide film that would result in the product becoming completely useless. At the higher reduction temperature, Mossbauer Spec data shows that as the salt is reduced and metallic iron is formed, the metal partially dissolves into the carbon. Carbon grading to cast iron and iron carbide grading to elemental iron in a couple of different crystal forms can be observed. As a consequence, there is an interaction between the carbon and the metal that creates unique properties that commercial ZVI does not have. Because of this interaction, the metallic iron is stable in contact with groundwater (GW) and can remain active for an extended time. Data has been collected showing activity beyond 8 years when in contact with water and the presence of trace dissolved oxygen has not mattered. This is important because iron powder and nano-scale ZVI in particular do not remain active in contact with groundwater for extended periods. In addition, the supported catalyst can degrade compounds that ZVI cannot or is very poor at. For example, the supported catalyst can degrade carbon tetrachloride and chloroform rapidly without significant generation of methylene chloride. It can readily degrade vinyl chloride and is effective with compounds like 1,1-DCA and 1,2-DCA.

It should also be understood, though, that there are a number of limitations to use of this supported catalyst. Reaction of the metallic iron embedded within the pore structure with halogenated organic compounds consumes the iron. This is referred to as the "iron demand" and is dependent on the specific compound. For example, the iron demand for carbon tetrachloride is substantially higher than that for vinyl chloride. Because the metallic iron is depleted and there are limits to the weight percent of iron that can realistically be loaded within the pore structure of the carbon, this results in an upper constraint on the amount or mass of the halogenated compound that can be degraded by a unit weight of impregnated carbon. As a result, when the soil concentrations of various halogenated compounds exceed approximately 1,000 ppm, the cost for treatment becomes high and treatment of DNAPL can be significant. Additionally, some compounds, such as chlorobenzenes and fluorinated compounds (e.g., fire retardants and perfluorooctanoic acid (PFOA)), are resistant to degradation by this material.

To understand the desirability and usefulness of the presently described compositions, it may now be useful to more fully discuss biological degradation of halogenated compounds. In general, whenever you have the following conditions: Microorganisms+electron donors+electron acceptors+nutrients, biological activity will occur that can potentially degrade contaminants and promote growth. There are many reactions that can occur, but they can be grouped into the following classifications: (a) use of the organic compound as a primary growth substrate; (b) growth promoting biological oxidation; (c) growth promoting biological reduction; (d) fermentation; and (e) cometabolism.

The first group classification or group includes pathways such as reductive dehalogenation and halorespiration. Fermentation is an important mechanism as this is one of the primary means for generation of hydrogen which is an important electron donor and takes part in numerous pathways resulting in replacement of hydrogen for chlorine on these halogenated compounds. In this process, chlorine atoms are displaced by hydrogen forming a host of daughter products. Common pathways shown in the literature for degradation of say TCE into a host of less chlorinated compounds like DCEs and VC are typically through reductive dechlorination. Fermentation may have a number of indicators. For example, generation of methane is strong evidence that fermentation is occurring as is generation of fatty acids. Aside from hydrogen and methane, a variety of fatty acids are produced by fermentation including acetate, formate, lactate, succinate, propionate, and butyrate. Once fatty acids are present, secondary fermentation may commence that consumes C3 and higher acids to yield additional acetate, formate, water, and hydrogen.

Cometabolism is a process by which the halogenated contaminant is degraded through enzymes and cofactors employed by the organism for metabolism of some other primary substrate (electron donor). Lactate is commonly used in this way for bioremediation of chlorinated solvents in concert with DHC and other organisms effective at degradation of such compounds. Many other materials have been employed for this purpose ranging from agricultural waste like corn cobs to crab and shrimp shells (chitin) to polymers like polylactates. Chitin is a material essentially insoluble in water but has been shown to be an effective platform or composition for degradation of chlorinated solvents using one or more microorganisms.

There are several key features of bioremediation. Naturally occurring microorganisms are typically able to degrade a wide spectrum of contaminants. In many cases, metabolic byproducts are also toxic contaminants; however, these compounds are also susceptible to biodegradation. For the most part, microorganisms are fairly robust being able to thrive in a wide range of conditions including pH, temperature, and salinity (but, note, there are exceptions to this rule). Essential nutrients such as trace metals are often available from the mineral content of subsurface soils. Alternative platforms or compositions are often advantageous and are widely used to promote the degradation of contaminants of concern. One common platform or composition used for this purpose is lactic acid.

There are, however, a number of limitations of bioremediation. Microorganisms often are unable to completely transform toxic contaminants into harmless byproducts. For example, some highly useful organisms convert TCE into vinyl chloride but are not able to degrade the vinyl chloride. As a result, other means are needed to deal with the vinyl chloride. One limitation of lactate is that it is water soluble such that it tends to move with groundwater and is rapidly consumed. As a result, supplemental doses of lactate are typically applied in practice to maintain a persistent concentration supportive of the degradation pathways. Other platforms or compositions such as vegetable oil or emulsified oils ferment slowly, and a high percentage of this activity is not beneficially captured to degrade targeted contaminants. Some organisms are difficult to handle and sensitive to subsurface conditions such as pH. Since contaminants are typically used as electron donors by the organisms (food source), as contaminant concentrations fall the microbial populations fall off and remedial progress stalls.

With all this in mind, the inventor has designed and fabricated a composition that is effective in combining biological degradation of halogenated compounds with an absorbent impregnated with metallic iron. It should be understood that the product (supported catalyst or elemental iron-based composition as labeled herein) made by impregnating the inner pore structure of activated carbon with metallic iron is very effective at degrading many halogenated compounds. Further, the rate of degradation of these compounds is very rapid. The activated carbon concentrates the contaminants, which enables effective contact with a very active and large metallic surface area. Nearly all of the absorption of organic compounds by the carbon will be within the micro-porous structure. Microorganisms will tend to inhabit the macro and meso-pore structure of the carbon as they are too large for access to the micro-pores.

The active metallic iron also resides within the micropores and so it would be expected that absorbed contaminants will rapidly react with the iron and very little biological degradation would be possible since the microbes are limited to the larger pores. If this were the case, then halogenated compounds would simply react with the available iron until it is depleted and residual contaminant residing within the micro-pores will slowly desorb over time. Such a process would severely limit the biological degradation rendering it nearly ineffective. Two essential features are missing from the above discussion. First is the fact that carbon and iron are conductors, and there is an additional interaction between them due to the iron partially dissolving into the carbon. The metabolic (biological process) process involves both electron donors and acceptors. Thus, there is a transfer of electrons during degradation or respiration of these halogenated compounds and the carbon and iron can facilitate this process. Recent work has shown that activated carbon can effectively shuttle electrons to absorbed compounds. The iron impregnated carbon will provide an even more effective platform for the shuttling of electrons.

The second missing feature has to do with whether absorbed compounds are bioavailable. In other words, it must be determined whether microorganisms residing within the macro and meso-pore structure of the carbon affect compounds stored within the microporous structure. Research performed by the inventor has produced definitive data proving that compounds absorbed by activated carbon are degraded by microorganisms residing in the larger pore network. When these two features are combined, the result is a highly effective and efficient system for degradation of halogenated compounds. Microorganisms secrete cofactors and enzymes that are able to penetrate into the microporous structure of the carbon and the metallic iron/carbon platform provides the shuttle for transport of electrons to complete the reaction. In this process, the iron is not consumed as it is if abiotic dechlorination reactions are in play. The net effect of this is that the rapid depletion of metallic iron within the pore structure of the carbon does not occur because of the electron shuttle created to fuel the biological degradation of absorbed compounds. There is, in effect, a very efficient system to catalyze the biological degradation pathways over depletion of the metallic iron.

The inventor then understood that the last piece of the puzzle has to do with providing an effective time release mechanism or platform to generate suitable fuels to support this process over time. Currently, materials that stem from low molecular weight fatty acids such as lactic acid or emulsified oils are utilized to facilitate bioremediation. However, neither of these or other materials in common use are well suited to support degradation over an extended period of time in an efficient manner. Simple addition of a complex carbohydrate or other organic compound is not enough as those microorganisms adept at degrading halogenated compounds are not typically suited to the breakdown or fermentation of such materials. As a result, the process is slow at best and, in many cases, nonexistent.

The key identified by the inventor is to add one or more organisms whose main function is degradation of organic compounds or polymeric substances (e.g., complex carbohydrates such as starch and cellulosic materials). When this is done, the organic compounds or polymeric substances (e.g., complex carbohydrates such as food grade starch) begin to function as time release platforms (or fuel supplied) or compositions because the large molecules are broken down into small pieces that are now directly usable for beneficial degradation of halogenated compounds. Although chitin was shown to perform in this system, it is virtually insoluble in water, and its structure is very much like cellulose. Cellulose is difficult to breakdown and was recently the focus of the biofuels industry and a concerted effort was put into fermenting this abundant material into ethanol. This proved to be more difficult than envisioned and chemical rather than biological means have been commercialized for production. The search for acceptable microorganisms continues and one of the more promising avenues involves looking for organisms in the feces of animals that eat cellulose such as the panda who survives mainly by consuming bamboo. Another limitation of chitin is that it is a byproduct of the fishing industry, being made from crab and shrimp shells. Fishing for these creatures is a seasonal activity and so the availability of chitin is not necessarily always dependable.

Among the many organic compounds tested, starch (e.g., corn or potato starch or other food grade starch) produced the best overall results. Food grade starch is readily available and inexpensive. Starch is slightly soluble in water and is readily fermented by a range of non-pathogenic organisms. For these reasons, starch is one preferred polysaccharide (or organic compound or polymeric substance) for use in the described system or as part of a platform for bioremediation organisms. In general, many other complex carbohydrates may be used, and the complex carbohydrate may be a polymer with a formula of $C_m((H_2O)_n)$, wherein m and n are different integers and wherein m is greater than 6 such as greater than 12. Starch-containing materials such as corn cobs and potatoes may be utilized. However, all of these "starch containing" materials suffer from the fact that they consist primarily of cellulosic material and suffer from the associated limitations thereof. For purposes of this invention, such materials could be used; however, they likely will not be as effective as food grade starch. For example, in one test, measurement of chloride demonstrated that the ratio of biological to chemical (abiotic) degradation was approximately 1.3:1. Further research may be useful to further increase this ratio and extend the life expectancy of the impregnated iron. It is expected that this system can be applied to a wide range of site conditions and was specifically developed to target source area impacts. Further, although not considered examples of complex carbohydrates, oligosaccharides (such as raffinose and stachyose, which are found in beans, cabbage, and the like) may be used along with or, in some cases, in place of one or more complex carbohydrates.

Representative examples of organisms (or microorganisms that may be used to provide a first bioremediation material as called out in the following claims) that degrade halogenated compounds fall into several metabolic groups including (but not limited to): halorespirators; acetogens; methanogens; and facultative anaerobes. Examples of halorespirators include Dehalococcoides strains (SiRem of Canada offers a consortia of these called KB-1), *Dehalobacter restrictus*, and *Deesulfitobacterium dehalogenans*. Examples of acetogens include *Clostridium aceticum* and *Bacillus acetogens*. Examples of methanogens include *Methanobacterium bryantii, Methanococcus deltae, Methanogenium cariaci*, and *Methanosarcina acetivorans*. Also, many methanogens are found among the Archea (e.g., there are over 50 described species). Examples of facultative anaerobes include bacterial and fungal genera such as *Actinomyces, Bacteroides, Clostridium, Porphyromonas*, and *Veillonella* species. Of course, one skilled in the art will readily understand that the above examples are a few of many microorganisms that are known and may be included singly or in combination in the first bioremediation material.

As discussed above, there are many types of starch (or food grade starch) with sources such as potato, corn, maize, rice, tapioca, wheat, soybean, and plants (or plant products). Likewise, a variety of organisms may be used alone or in combination in the second bioremediation material (as called out in the claims) to provide useful degradation of such starches. Two common breakdown products of the biological degradation of starch are maltose and glucose. Examples of bacteria that may be provided in the second bioremediation material include: *Bacillus amyloliquefaciens, Bacillus licheniformis, Bacillus subtilis*, and *Pseudomonas* spp. Further, examples of fungi that may be provided in the second bioremediation material include: *Aspergillus niger* and *Penicillium*.

The foregoing description is considered as illustrative only of the principles of the compositions and methods described and later claimed. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. Furthermore, since a number of modifications and changes will readily occur to those skilled in the art, it is not desired to limit the invention to the exact construction and process shown described above. Accordingly, all suitable modifications and equivalents may be resorted to falling within the scope of the invention as defined by the claims that follow.

For example, one preferred implementation provides a remediation composition with an adsorbent impregnated with a reducing agent for adsorbing at least one halogenated compound. The term "reducing agent" is intended to include all metals, alloys, and a range of other materials at provide reducing functionality such as, but not limited to, one or more sulfides. Further, the composition includes a first set of one or more microorganisms able to degrade the at least one halogenated compound. To provide a time release quality, the composition includes at least one polyamide or at least one polysaccharide, or a polypeptide (with polypeptides likely being useful as a substitute for starch or as a supplemental material to create time release of nitrogen, which can be vital for cell growth) and a second set of one or more microorganisms breaking the at least one polyamide, at least one polysaccharide, or at least one polypeptide into smaller molecules or compounds useful to the first set of one or more microorganisms during degradation of the halogenated compound. Note, the composition may include a combination of one or more polyamides, polysaccharides, and polypeptides (e.g., with "or" meaning at least one of these three materials but could contain two of the materials or all three of the materials).

The second set of or more microorganisms (e.g., algae, fungi, bacteria, archaea, or one or more unicellular organisms) degrades the at least one polyamide, at least one polysaccharide, or at least one polypeptide over a period of time. Further, the smaller molecules or compounds donate electrons for use by the first set of one or more microorganisms during the degradation of the set of halogenated compounds, whereby in combination the at least one polyamide, at least one polysaccharide, or at least one polypeptide and the second set of one or more microorganisms provide a time release platform fueling the degradation by the first set of one or more microorganisms. In some embodiments, the adsorbent is activated carbon and the reducing agent is an alloy, a sulfide, and/or a metal. In particular cases, the reducing agent is a metal, such as elemental iron, that is impregnated into the activated carbon by being at least partially dissolved into walls of pores of the activated carbon. Then, transitions in the walls of the pores between the activated carbon and the elemental iron may be cast iron and iron carbide.

The composition may be formed to have a time-release period greater than 20 days. The at least one polyamide, at least one polysaccharide, or at least one polypeptide may take the form of food grade starch or chitin (or a combination thereof). In other cases, though, the at least one polyamide, at least one polysaccharide, or at least one polypeptide is made up of shredded wool or feathers (or both).

I claim:

1. A remediation composition, comprising:
   an adsorbent for adsorbing at least one halogenated compound, wherein the adsorbent is impregnated with a metal;
   a first set of one or more microorganisms able to degrade at least one halogenated compound, wherein the first set of one or more microorganisms includes acetogens; and
   a time release compound, combined with the first set of one or more microorganisms, comprising:
   a polymeric substance comprising at least one of a polyamide, a polypeptide, and a polysaccharide; and
   a second set of one or more microorganisms mixed with the polymeric substance, wherein the second set of one or more microorganisms degrades, over a period of time, the polymeric substance into smaller molecules or compounds that donate electrons for use by the first set of one or more microorganisms during degradation of the halogenated compound and wherein the period of time has a length of at least 20 days.

2. The composition of claim 1, wherein the second set of one or more microorganisms includes bacteria including at least one of *Bacillus amyloliquefaciens, Bacillus licheniformis, Bacillus subtilis*, or *Pseudomonas* spp.

3. The composition of claim 1, wherein the second set of one or more microorganisms includes fungi.

4. The composition of claim 3, wherein the fungi comprises at least one of *Aspergillus niger* and *Penicillium*.

5. The composition of claim 1, wherein the second set of one or more microorganisms comprises algae.

6. The composition of claim 1, wherein the adsorbent comprises activated carbon and the metal comprises elemental iron.

7. The composition of claim 6, wherein the elemental iron is impregnated into the activated carbon by being at least partially dissolved into walls of pores of the activated carbon and wherein transitions in the walls of the pores between the activated carbon and the elemental iron comprises cast iron and iron carbide.

8. A remediation composition, comprising:
   an adsorbent for adsorbing at least one halogenated compound, wherein the adsorbent is impregnated with a metal;
   a first set of one or more microorganisms able to degrade at least one halogenated compound, wherein the first set of one or more microorganisms includes methanogens; and
   a time release compound, combined with the first set of one or more microorganisms, comprising:
   a polymeric substance comprising at least one of a polyamide, a polypeptide, and a polysaccharide; and
   a second set of one or more microorganisms mixed with the polymeric substance, wherein the second set of one or more microorganisms degrades, over a period of time, the polymeric substance into smaller molecules or compounds that donate electrons for use by the first set of one or more microorganisms during degradation of the halogenated compound and wherein the period of time has a length of at least 20 days.

9. The composition of claim 8, wherein the second set of one or more microorganisms includes bacteria including at least one of *Bacillus amyloliquefaciens, Bacillus licheniformis, Bacillus subtilis*, or *Pseudomonas* spp.

10. The composition of claim 8, wherein the second set of one or more microorganisms includes fungi.

11. The composition of claim 10, wherein the fungi comprises at least one of *Aspergillus niger* and *Penicillium*.

12. The composition of claim 8, wherein the second set of one or more microorganisms comprises algae.

13. The composition of claim 8, wherein the adsorbent comprises activated carbon and the metal comprises elemental iron.

14. The composition of claim 13, wherein the elemental iron is impregnated into the activated carbon by being at least partially dissolved into walls of pores of the activated carbon and wherein transitions in the walls of the pores between the activated carbon and the elemental iron comprises cast iron and iron carbide.

15. A remediation composition, comprising:
   an adsorbent for adsorbing at least one halogenated compound, wherein the adsorbent is impregnated with a metal;
   a first set of one or more microorganisms able to degrade at least one halogenated compound, wherein the first set of one or more microorganisms includes facultative anaerobes;
   and a time release compound, combined with the first set of one or more microorganisms, comprising:
   a polymeric substance comprising at least one of a polyamide, a polypeptide, and a polysaccharide; and
   a second set of one or more microorganisms mixed with the polymeric substance, wherein the second set of one or more microorganisms degrades, over a period of time, the polymeric substance into smaller molecules or compounds that donate electrons for use by the first set of one or more microorganisms during degradation of the halogenated compound and wherein the period of time has a length of at least 20 days.

16. The composition of claim 15, wherein the second set of one or more microorganisms includes bacteria including at least one of *Bacillus amyloliquefaciens, Bacillus licheniformis, Bacillus subtilis*, or *Pseudomonas* spp.

17. The composition of claim 15, wherein the second set of one or more microorganisms includes fungi.

18. The composition of claim 17, wherein the fungi comprises at least one of *Aspergillus niger* and *Penicillium*.

19. The composition of claim 15, wherein the second set of one or more microorganisms comprises algae.

20. The composition of claim 15, wherein the adsorbent comprises activated carbon and the metal comprises elemental iron.

21. The composition of claim 20, wherein the elemental iron is impregnated into the activated carbon by being at least partially dissolved into walls of pores of the activated carbon and wherein transitions in the walls of the pores between the activated carbon and the elemental iron comprises cast iron and iron carbide.

* * * * *